United States Patent [19]

Cracauer et al.

[11] Patent Number: 4,804,628

[45] Date of Patent: Feb. 14, 1989

[54] HOLLOW FIBER CELL CULTURE DEVICE AND METHOD OF OPERATION

[75] Inventors: Ray F. Cracauer, Minneapolis; Robert D. Walker, Ham Lake; Micheal L. Gruenberg, Coon Rapids, all of Minn.

[73] Assignee: Endotronics, Inc., Coon Rapids, Minn.

[21] Appl. No.: 88,463

[22] Filed: Aug. 19, 1987

Related U.S. Application Data

[63] Continuation of Ser. No. 658,549, Oct. 9, 1984, abandoned.

[51] Int. Cl.[4] .......................... C12N 5/00; C12M 3/00; C12M 1/14; C02F 1/44
[52] U.S. Cl. ............................. 435/240.242; 435/285; 435/310; 210/323.2; 210/321.8; 210/500.23
[58] Field of Search ................. 435/240.242, 310, 284, 435/285, 948; 210/321.1, 323.2, 335, 433.2, 650, 651, 806; 436/178

[56] References Cited

U.S. PATENT DOCUMENTS

| | | | |
|---|---|---|---|
| 3,407,120 | 10/1968 | Weiss et al. | 195/104 |
| 3,598,728 | 8/1971 | Bixler et al. | 210/22 |
| 3,734,851 | 5/1973 | Matsumura | 210/22 |
| 3,767,790 | 10/1973 | Guttag | 424/81 |
| 3,821,087 | 6/1974 | Knazek et al. | 195/127 |
| 3,827,565 | 8/1974 | Matsumura | 210/22 |
| 3,883,393 | 5/1975 | Knazek et al. | 195/1.8 |
| 3,911,140 | 10/1975 | Osborne et al. | 426/36 |
| 3,997,396 | 12/1976 | Delente | 195/1.8 |
| 4,087,327 | 5/1978 | Feder et al. | 195/1.7 |
| 4,181,604 | 1/1980 | Onishi et al. | 210/8 |
| 4,184,922 | 1/1980 | Knazek et al. | 435/284 |
| 4,200,689 | 4/1980 | Knazek et al. | 435/2 |
| 4,201,845 | 5/1980 | Feder et al. | 195/127 |
| 4,206,015 | 6/1980 | Knazek et al. | 435/2 |
| 4,220,725 | 9/1980 | Knazek et al. | 435/285 |
| 4,242,460 | 12/1980 | Chick et al. | 435/284 |
| 4,266,026 | 5/1981 | Breslau | 435/182 |
| 4,377,639 | 3/1983 | Lee | 435/285 |
| 4,391,912 | 7/1983 | Yoshida et al. | 435/241 |
| 4,396,510 | 8/1983 | Hsei | 210/321.3 |
| 4,440,853 | 4/1984 | Michaels et al. | 435/68 |
| 4,442,206 | 4/1984 | Michaels et al. | 435/68 |

Primary Examiner—John Tarcza
Attorney, Agent, or Firm—Kinney & Lange

[57] ABSTRACT

An improved cell culturing device includes a hollow fiber cartridge having a shell and a plurality of capillaries extending through the shell with at least some of the capillaries having selectively permeable walls. A cell culturing space is located between the shell and capillaries. The improvement includes a chamber containing a second medium supply fluidly connected to the cell culturing space. A pressurizing system pressurizes the medium within the chamber to a level higher than the level of medium flowing through the lumen of the capillaries. A valving mechanism alternatively and selectively restricts flow of medium between the chamber and the cell culturing space through first and second conduits such that circulation is effected in the cell culturing space.

21 Claims, 2 Drawing Sheets

HOLLOW FIBER CELL CULTURE DEVICE AND METHOD OF OPERATION

This is a continuation of U.S. patent application Ser. No. 658,549, filed Oct. 9, 1984 and now abandoned.

REFERENCE TO CO-PENDING APPLICATIONS

Reference is hereby made to the following copending patent application filed on even date herewith and assigned to the same assignee: "Hollow Fiber Culture Device for Improved Nutrient Perfusion and Product Concentration and Method of Operation" Ser. No. 658,550.

BACKGROUND OF THE INVENTION

1. Field of the Invention

The present invention relates to cell culturing devices, and in particular, it relates to cell culturing devices having a plurality of hollow fiber membranes that efficiently and selectively transfer oxygen, nutrients and other chemical stimuli and remove waste products to grow and maintain cells in vitro at high cell densities to provide high yields of product formation per unit reactor volume.

2. Description of the Prior Art

Cell culture devices for culturing cells in vitro having a shell with a plurality of hollow fiber membranes have been known for quite some time. Medium containing oxygen, nutrients and other chemical stimuli is transported through the lumen of the hollow fiber membranes and undergoes a pressure drop resulting in an outward radial convective flow at the entry port of the device and an inward flow at the exit port of the device. Cells are grown in the fluid space between the fibers and the shell wall.

Hollow fiber culture devices have been proven to be ideal for the maintenance of many types of cells at high densities in vitro. The mass transfer characteristics of hollow fiber culture devices provide an efficient means of delivering nutrients and removing waste products from a culture. The semi-porous hollow fiber membranes can be selected with various pore sizes. With proper pore size selection, the cellular product can be maintained on the outside of the fibers, while waste products and contaminating proteins will pass through the membrane pores into the lumen of the hollow fibers where they can be subsequently removed from the culture.

To economically produce cell-derived products in a hollow fiber culture device, large numbers of the cells must be maintained viable in optimal culture conditions for product formation over long periods of time. Prior art hollow fiber culture devices have many limitations that prevent their use in the economical production of cell-derived products in commercial quantities. These limitations include: (1) formation of gradients in the cell compartment; (2) inability to directly monitor and control cellular environment; (3) lack of fluid movement in cell compartment leads to microenvironment formation around cells; (4) fibers are not equidistant apart in culture device leading to anoxic or dead spaces; (5) efficient mass transfer becomes difficult at high cell densities; and (6) the pressure drop across the device increases as the device is scaled up, increasing the problems cited above, thus limiting scaleability. The purpose of the present invention is to overcome these limitations, making it possible to utilize a hollow fiber culture device for the economical production of cell-derived products. The following explains each of the prior art limitations in more detail.

1. Formation of Gradients in the Cell Compartment.

Formation of gradients of nutrients, pH, $O_2$, $CO_2$, lactic acid, ammonia and other components of the culture media in the cell compartment is a common problem in hollow fiber culture devices. The gradients form due to the manner in which nutrient media flows through the device. Nutrients are more available to the cells near the inlet port due to the outward flow from the hollow fibers. As media flows to the outlet, metabolic waste products, such as lactic acid and ammonia, accumulate in the cell compartment undesirably affecting cell viability.

2. Inability to Monitor and Control Cell Compartment.

Because of the nature of prior art hollow fiber cartridges, it is not possible to incorporate monitoring devices into the cell compartment. Thus, maintenance of optimal culture conditions is very difficult. The only control over the cell compartment environment is by diffusion of products from the lumen of the hollow fibers to the cell compartment.

3. Formation of Microenvironments.

Very little fluid motion occurs in the cell compartment of prior art hollow fiber culture devices. This leads to microenvironments forming around quickly metabolizing cells, adversely affecting other cells in the device by altering pH.

4. Formation of Anoxic Pockets.

Hollow fibers are packed into cartridges. Usually the fibers are not equidistant apart and thus, some cells are farther away from the nutrient source than others. This leads to pockets where cells will die due to lack of oxygen or failure of nutrients to reach the cells by diffusion.

5. Mass Transfer Limitations.

As the cells grow to high cell densities, nutrients must diffuse through greater layers of cells. Mass transfer by diffusion is limited, limiting the number of cells that can be maintained in the culture device.

6. Pressure Drop.

Hollow fiber culture devices perfuse cells in the cell compartment and remove waste products due to the forces set up by the pressure drop that occurs across the cartridge. This pressure drop becomes greater as the length of the fibers are increased. This pressure drop also creates the gradient problems described above. Thus, the length of the fibers is limited by the pressure drop which enhances the gradient problem.

Some examples of prior art cell culturing devices are described in the following patents:

| Inventor | U.S. Pat. No. |
|---|---|
| Matsumura | 3,734,851 |
| Knazek et al | 3,821,087 |
| Knazek et al | 3,883,393 |
| Osborne et al | 3,911,140 |
| Delente | 3,997,396 |
| Feder et al | 4,087,327 |
| Knazek et al | 4,184,922 |
| Knazek et al | 4,200,689 |
| Feder et al | 4,201,845 |
| Knazek et al | 4,206,015 |
| Knazek et al | 4,220,725 |
| Chick et al | 4,242,460 |
| Yoshida et al | 4,391,912 |
| Hsei | 4,396,510 |

| Inventor | U.S. Pat. No. |
| --- | --- |
| Michaels et al | 4,440,853 |
| Michaels et al | 4,442,206 |

SUMMARY OF THE INVENTION

The present invention includes an improved culturing device and method of culturing cells in vitro. The device includes a hollow fiber cartridge having a shell with a plurality of capillaries extending therethrough with at least some of the capillaries having selectively permeable membrane walls. A first supply of medium is delivered to the capillaries at a first selected pressure and flow rate. A cell culturing space is defined between the shell and the capillaries. The improvement includes a chamber having a second supply of medium in the chamber is pressurized to a level greater than the medium flowing through the lumen of the capillaries. A valving mechanism is disposed to selectively and alternatively restrict the flow of the second supply of medium through first and second conduits, respectively, that connect the chamber with the cell culturing space such that circulation of fluid within the cell culturing space is effected.

DETAILED DESCRIPTION OF THE PREFERRED EMBODIMENTS

Figure 1:
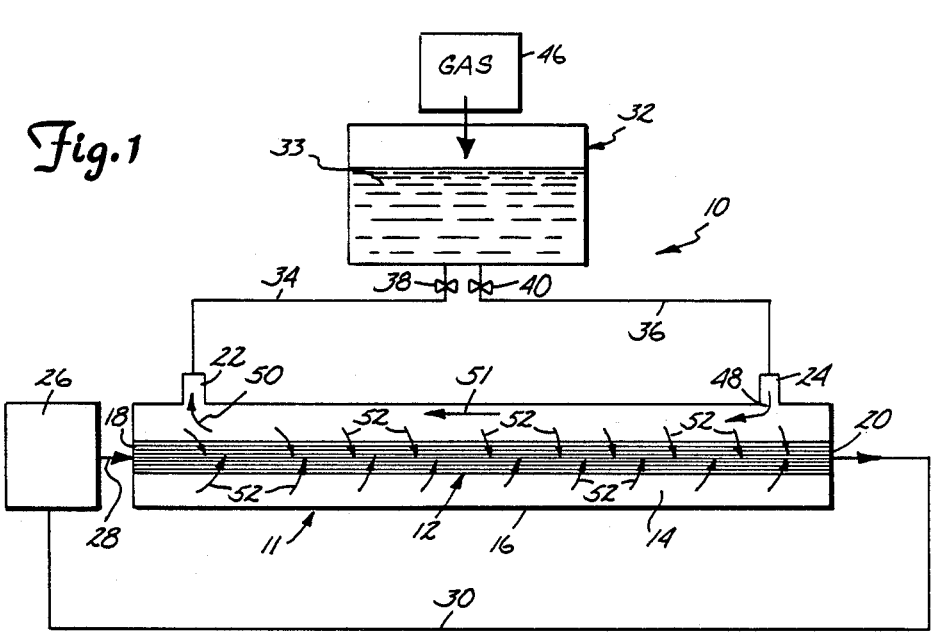
FIG. 1 is a diagrammatical view of an improved cell culturing device of the present invention.

The apparatus of the present invention is diagrammatically illustrated in FIG. 1. The improved cell culturing device includes a cell culturing unit such as a hollow fiber cartridge 11 in which cells are maintained and grown. The hollow fiber cartridge 11 includes a plurality of capillaries, generally indicated at 12 extending through a shell 16. Each capillary includes a lumen (not shown) through which medium containing oxygen, nutrients and otehr chemical components is transported. The oxygen, nutrients and other chemical components contained in the medium diffuse through membrane walls of the capillaries into an extracapillary space 14 containing cells which are to be maintained. The extracapillary space 14 is defined as the space between the shell 16 and the capillaries 12. Typically, the capillaries are disposed in a bundle which extends from an input end 18 to an output end 20 of the cartridge. A commercially-available cartridge suitable for use in the device of the present invention is made by Amicon Corporation of Danvers, Mass.

The cartridge 11 further includes first and second spaced-apart ports 22 and 24, respectively. Preferably, the first and second ports 22 and 24 are spaced apart so that the port 22 is located proximate the front end of the cartridge and the port 24 is located proximate the back end of the cartridge. Both ports are in fluid communication with the extracapillary space 14.

Types of cells that are suitable for in vitro culturing in the device of the present invention include bacteria, yeast and fungi that are naturally occurring or are modified by conjugation or genetic engineering techniques, such as transformation, DNA insertions, transduction, fusion and the like. In addition, primary and transformed mammalian cells (including mammalian cells altered by genetic engineering techniques and virus formation), tumor cells, hybridomas and other fused cells are well suited for culturing in the device of the present invention.

A delivery system 26 delivers a primary medium supply through suitable conduit 28 to the lumen of the capillaries 12. The medium exits the cartridge into suitable tubing 30 that forms a recirculation line returning the medium back to the delivery system 26.

The delivery system 26 delivers medium at a selective rate and pressure. Suitable delivery systems are well known in the art. Suitable delivery systems are described in application Ser. No. 350,135 filed on Feb. 19, 1982, application Ser. No. 388,136 filed on June 14, 1982, and application Ser. No. 483,284 filed on Apr. 8, 1983, all assigned to the same assignee as the present application and which are hereby incorporated by reference.

An expansion chamber 32 is fluidly connected to the extracapillary space 14 through conduit 34 connected to the first port 22 and conduit 36 connected to the second port 24. First and second valves 38 and 40 are operably disposed to restrict flow between the extracapillary space 14 and the expansion chamber 32 within the conduits 34 and 36, respectively. In one working example, the conduits 34 and 36 include flexible tubing and the valves 38 and 40 are pinch-type valves which pinch the tubing to stop flow therethrough.

The expansion chamber 32 contains a second supply of medium 33. The medium supply 33 is selectively pressurized at a substantially constant level by a pressurizing system 46. In one working embodiment of the present invention, the pressurizing system 46 is a gas system that delivers an oxygen containing gas under pressure to the chamber 32.

The pressure in the expansion chamber 32 is kept at a higher pressure than the pressure within the lumens of the capillaries 12. The valves 38 and 40 are alternatively closed and opened to create circulation within the extracapillary space 14. For example, when valve 40 is opened and valve 38 is closed, flow of medium occurs through tubing 36 and into extracapillary space 14 through port 24, as indicated by arrow 48. Then valve 38 is opened and valve 40 is closed and flow occurs in the direction of arrow 50 through port 22 and through the tubing 34 into the expansion chamber 32. The positions of the valves are alternated such that circulation of fluid within the extracapillary space 14 is effected in the clockwise direction of arrow 51. The circulation is in a pulsatile form, with the valves 38 and 40 being opened and closed momentarily.

Producing the circulation within the extracapillary space 14 eliminates the formation of gradients of nutrients, pH, $O_2$, $CO_2$, lactic acid, ammonia and other components in the extracapillary space that were a problem in the prior art. Microenvironments formed by quickly metabolizing cells are greatly minimized since circulation is effected in the extracapillary space. In addtion, circulation in the extracapillary space minimizes the gradient problems caused by the pressure drop that had occurred across prior art cartridges.

Figure 2:
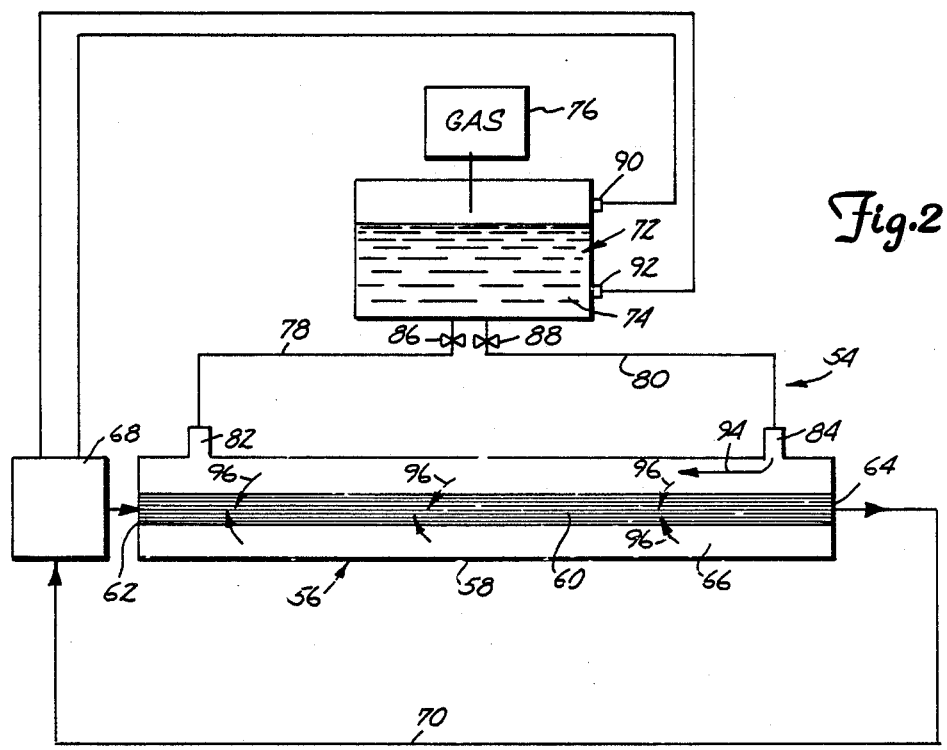
FIG. 2 is a diagrammatical view of an alternative embodiment of the cell culturing device of the present invention.

An alternative embodiment 54 of the device of the present invention is diagrammatically illustrated in FIG. 2. The embodiment 54 similarly includes a hollow fiber cartridge 56 having a shell 58 and a plurality of semi-permeable capillaries 60 extending from the forward end 62 to a rearward end 64. An extracapillary space 66 is defined between the capillaries 60 and the shell 58. A delivery system 68 delivers a supply of medium at a selected pressure and flow rate to the lumens of the capillaries 60 similar to the delivery system 26 discussed previously. The medium is circulated from the outlet end 64 of the hollow fiber cartridge through tubing 70 back to the delivery system 68.

A chamber 72 contains a second supply of medium 74 that is pressurized at a substantially constant level by a gas pressurizing system 76. The chamber 72 is fluidly connected by tubing 78 and 80 to the extracapillary space 66 through ports 82 and 84, respectively. Valves 86 and 88 are operably connected to the conduits 78 and 80, respectively, so that flow may be selectively restricted in either the tubing 78 or 80.

The chamber 72 includes an upper level sensor 90 and a lower level sensor 92 that deliver a signal to the delivery system 68. When the upper sensor 90 senses a high level of medium within the chamber, the pressure under which the delivery system 68 is delivering medium to the capillaries 60 is lowered to a valve less than the pressurization of the chamber 72 and sufficient to cause ultrafiltrative conditions. When a low level is sensed by the sensor 92, the delivery system increases the pressure that the medium is delivered under ultrafiltrative conduits through the capillaries to increase the amount of medium within the chamber 72.

Figure 3:
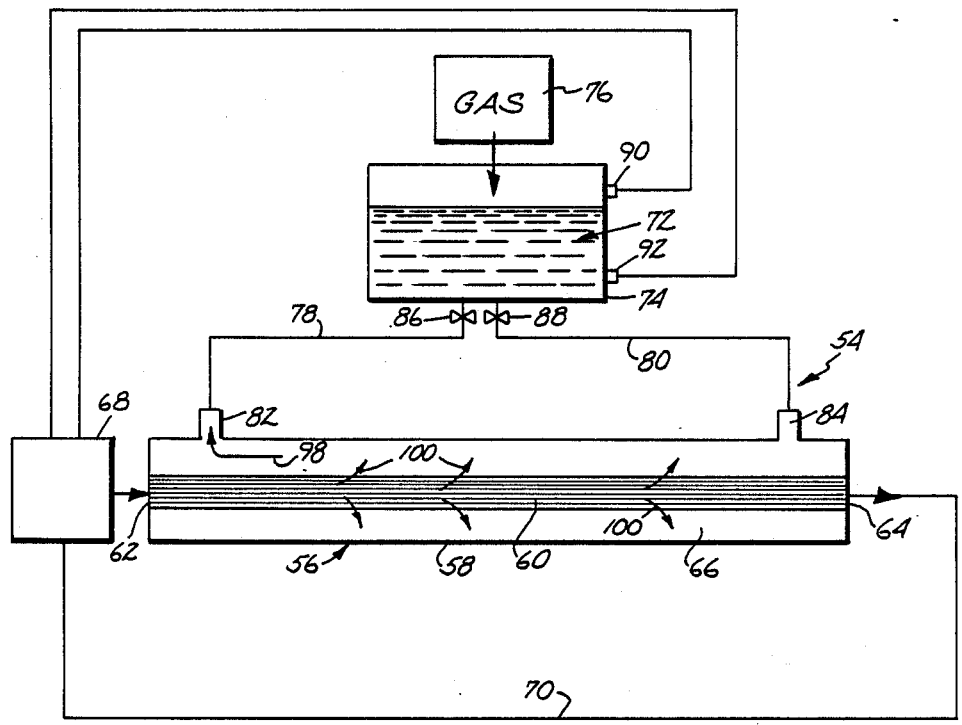
FIG. 3 is a diagrammatical view of still another alternative embodiment of the cell culturing device of the present invention.

In operation, with valve 88 in the open position and valve 86 in the closed position, and the deliver system 68 delivering medium at a pressure less than the pressurization of the chamber 72, flow in the extracapillary space 66 is effected generally in the direction of arrow 94. Diffusion of waste products into the lumens of the capillaries 60 occurs as indicated by arrows 96. When the level within the chamber 72 falls past sensor 92, sensor 92 sends a signal to the delivery system 68 upon which the pressure of the medium being delivered to the capillaries 60 is raised above the level of pressurization within the chamber 72. The valve 86 is then opened and the valve 88 closed such that medium flows from the extracapillary space, through the port 82, into tubing 78 and back into the chamber 72, as initially indicated by arrow 98. Positive ultrafiltration perfusion of oxygen, $CO_2$, nutrients and other chemical components occurs through the walls of the capillaries 60, as indicated by arrow 100 in FIG. 3.

The above sequence is alternated such that circulation is effected in the extracapillary space. In addition, diffusion of waste products and other undesirable components back into the lumen of the capillaries and diffusion of oxygen, $CO_2$, nutrients and other chemical components into the extracapillary space is enhanced.

· In one example, the device of the present invention was used successfully to grow and maintain hybridoma cells that grew to cell densities of approximately $1 \times 10^8$ to $1 \times 10^9$ cells per milliliter and produced large quantities of a monoclonal antibody over a 90-day period. Typically, growing and maintaining hybridoma cells in a hollow fiber cartridge requires that the capillaries have membrane walls that have a selective molecular weight cut-off of less than approximately 50,000 Daltons. In the example, capillaries having a selective molecular weight cut-off of less than approximately 15,000 Daltons were used. The smaller molecular weight cut-off was used to significantly eliminate diffusion of the antibody being produced by the cells into the lumen of the capillaries. However, the decrease in the molecular weight cut-off increases resistance to oxygen transfer and nutrient transfer through the walls of the capillaries to the cells. In addition, there is increased resistance to waste product transfer (such as lactic acid produced by the cells) through the capillary walls into the lumen. A high wast product concentration is deleterious to the growth and maintenance of the cells.

It has been observed by the applicants in using the prior art hollow fiber cartridge arrangements, that an oxygen and nutrient concentration gradient formed across the length of the capillary bundle in the extracapillary space with a nutrient and oxygen build-up near the front end of the cartridge and a waste build-up near the back end of the cartridge. It is also believed that the build-up of nutrients and oxygen near the front end of the extracapillary space further added to the resistance of diffusion of oxygen and nutrients since the build-up decreases the concentration gradient across the capillary walls.

The expansion chamber had a medium volume approximately equal to the volume of the extracapillary space and was initially pressurized, for example, to a positive 100 millimeter of mercury. The valve 86 was opened while the valve 88 was closed. The delivery system 68 was operated to effect a pressure in the lumen of the capillaries of approximately 200 millimeters of mercury. The effect was that fluid flowed from the extracapillary space through tubing 78 into the expansion chamber and diffusion of $O_2$, $CO_2$, and nutrients into the extracapillary space.

When a high level of medium was sensed in the chamber, the pressure within the lumen of the capillaries was lowered below the pressure in the expansion chamber. The valve 88, previously closed, was opened while the valve 86, that was previously opened, was closed. The effect was that there was flow of medium from the expansion chamber 72, into the extracapillary space through tubing 80 and negative ultrafiltration of waste products.

The procedure was continued, alternating the relative pressure in the capillaries and alternating the position of the valves 86 and 88 to effect circulation of the medium through the cell culturing space 14 and positive ultrafiltration perfusion of desirable components into the extracapillary space and waste products out of the extracapillary space. It is believed that the effect of providing circulation in the cell culturing space enhances the environment in which the cells are grown. Nutrient and oxygen perfusion through the capillary membranes is increased when the pressure in the capillary lumen is greater than in the expansion chamber, and waste product diffusion through the capillary walls is enhanced when the pressure in the expansion chamber is greater than the pressure in the capillary lumen because the transfer is occuring under ultrafiltrative conditions. In addition, oxygen and nutrients are evenly distributed throughout the cell culturing space greatly increasing access to a much greater portion of the cells of both oxygen and nutrients.

It has also been observed that no significant difference in cell densities occurs whether a clockwise or counterclockwise circulation is effected between the extracapillary space 14 and the expansion chamber 32. A counterclockwise circulation is effected by closing valve 38 and opening valve 40 while the pressure in the expansion chamber 32 is less than the pressure in the lumen of the capillaries. When the pressure in the lumen of the capillaries is decreased while the pressure in the expansion chamber is increased to a level greater than in the lumen of the capillaries, valve 38 is open and valve 40 is closed.

The ultrafiltrative conditions created by the differential in pressure, both negative and positive, between the capillaries and the expansion chamber aids in the maintenance of high cell densities. Transport of oxygen and nutrients through the layers of cells is greatly enhanced. Removal of components that effect pH to the detriment of the cells is greatly increased under ultrafiltrative conditions.

Although the present invention has been described with reference to preferred embodiments, workers skilled in the art will recognize that changes may be made in form and detail without departing from the spirit and scope of the invention.

What is claimed is:

1. An improved cell culture device for in vitro cell growth, the device including a shell having first and second ends, first and second ports, and a plurality of capillaries extending between the first and second ends within the shell with at least some of said capillaries having selectively permeable walls, and cell culturing space being defined between the shell and the capillaries with the first and second ports in fluid communication therewith, a first supply of medium being delivered into the capillaries at a first selected pressure, the improvement comprising:
   a medium expansion chamber fluidly connected to the first and second ports and containing a second supply of medium at a second pressure;
   valving means for selectively restricting flow of the second supply of medium through the first and second ports into the culturing space, wherein the valving means operates such that flow of the second supply of medium is altered through the first and second ports to effect medium circulation within cell culturing space and enhance diffusion of waste products out of the culturing space and diffusion of medium components into the culturing space while retaining cells and desired cell products;
   pressurizing means for keeping the second pressure in the chamber approximately constant and maintaining the second pressure independently of the first pressure; and
   means for selectively raising and lowering the first pressure in the capillaries with respect to the second pressure in the chamber effecting circulation within the cell culturing space.

2. The device of claim 1 wherein the chamber is fluidly connected to the first and second ports of the shell by first and second conduits and wherein the valving means includes first and second valves controlling flow through the first and second conduits, respectively.

3. The device of claim 1 wherein the permeable walls of the capillaries have a selective molecular weight cut-off of less than approximately 50,000 Daltons.

4. The device of claim 3 wherein the permeable walls of the capillaries have a selective molecular weight cut-off of less than approximately 15,000 Daltons.

5. A cell culture device for in vitro cell growth, the device comprising:
   a hollow fiber cartridge having a shell with a plurality of capillaries extending between a fluid input end and a fluid output end and defining an extracapillary space between the shell and the capillaries with at least some of said capillaries having selectively permeable walls and the shell having first and second spaced-apart ports communicating with the extracapillary space;
   delivery means for transporting to the capillaries a first supply of medium and including first means for maintaining the first supply of medium in the capillaries at a first pressure that is selectively raised and lowered;
   a chamber fluidly connected to the first and second ports containing a second supply of medium and including second means for maintaining the second supply of medium at a selected second pressure;
   valving means for selectively controlling flow of the second supply of medium from the chamber through the first and second ports; and
   wherein the delivery means alternatively raises and lowers the first pressure in the capillaries above and below the second pressure in the chamber and wherein the first means for maintaining and the second means for maintaining control the first and second pressures independently of each other and in cooperation with the valving means such that circulation of medium within the extracapillary space is effected.

6. The device of claim 5 wherein the chamber is fluidly connected to the first and second ports of the shell by first and second conduits and wherein the valving means includes first and second valves restricting flow in the first and second conduits, respectively.

7. The device of claim 5 wherein the second means for maintaining includes a mechanism for delivering gas under pressure into the chamber.

8. The device of claim 5 wherein the permeable walls of the capillaries have a selective molecular weight cut-off of less than approximately 50,000 Daltons.

9. The device of claim 8 wherein the permeable walls of the capillaries have a selective molecular weight cut-off of less than approximately 15,000 Daltons.

10. A method for culturing cells in a hollow fiber cartridge having a shell and a plurality of capillaries extending through the shell, and defining a cell culturing space between the capillaries and shell with the cell culturing spce being fluidly connected to an expansion chamber through a first and second port, each with a valve, the capillaries being provided with a first supply of medium by a delivery system the method comprising:
   maintainng a first pressure through the first supply of medium in the capillaries;
   maintaining a second pressure through a second supply of medium in the cell culturing space independently of the first pressure; and
   alternatively increasing and decreasing the first pressure within the capillaries above and below the second pressure within the cell culturing space so that flow of medium from the cappilaries into the cell culturing space is effected when the first pressure in the capillaries is greater than the cell culturing space and flow of medium is effected from the cell culturing space in the capillaries when the first pressure is less than the second pressure, the alternating of the first pressure above and below the second pressure producing circulation in the cell culturing space.

11. The method of claim 10 wherein the first pressure is increased and decreased sufficiently to cause ultrfiltration of components from the medium through the capillary walls into the cell culturing space and ultrafiltration of components deleterious to cells in the cell culturing space into the lumen of the capillaries, respectively.

12. The method of claim 11 and further including establishing an upper level sensing point and a lower level sensing point in the expansion chamber and sensing when the medium has reached the upper level and the lower level; and increasing the pressure within the capillaries when the low level has been sensed and decreasing the pressure in the capillaries when the high level has been sensed.

13. An improved cell culture device for in vitro cell growth, the device including a shell having first and second ends, first and second ports, and a plurality of capillaries extending between the first and second ends within the shell with at least some of said capillaries having selectively permeable walls, and a cell culturing space being defined between the shell and the capillaries with the first and second ports in fluid communiation therewith, a first supply of medium being delivered into the capillaries at a first selected pressure, the improvement comprising:
- a chamber fluidly connected to the first and second ports and containing a second supply of medium independent of the first supply of medium for delivery at a second selected pressure;
- valving means for selectively restricting flow of the second supply of medium through the first and second ports into the culturing space, wherein the valving means is operated such that flow of the second supply of medium is alternated through the first and second ports to effect circulation within the cell culturing space and enhance diffusion of waste products out of the culturing space and diffusion of medium components into the culturing space;
- second pressurizing means for keeping the second pressure approximately constant;
- upper and lower level sensors disposed at a selected upper and lower level within the chamber to sense a lower level and an upper level of medium; and
- wherein the delivery means is selectively controlled along with the valving means to raise the first pressure in the capillaries with respect to the second pressure in the chamber when a low level is sensed and to lower the first pressure in the capillaries with respect to the second pressure in the chamber when a high level is sensed effecting circulation within the cell culturing space.

14. The device of claim 13 wherein the chamber is fluidly connected to the first and second ports of the shell by first and second conduits and wherein the valving means includes first and second valves controlling flow through the first and second conduits, respectively.

15. The device of claim 13 wherein the permeable walls of the capillaries have a selective molecular weight cut-off of less than approximately 50,000 Daltons.

16. The device of claim 15 wherein the permeable walls of the capillaries have a selective molecular weight cut-off of less than approximately 15,000 Daltons.

17. A cell culture device for in vitro cell growth, the device comprising:
- a hollow fiber cartridge having a shell with a plurality of capillaries extending between a fluid input end and a fluid output end and defining an extracapillary space between the shell and the capillaries with at least some of said capillaries having selectively permeable walls and the shell having first and second spaced-apart ports communicating with the extracapillary space;
- delivery means for transporting to the capillaries and for selectively raising and lowering a first pressure of a first supply of medium in the capillaries;
- a chamber fluidly connected to the first and second ports containing a second supply of medium;.
- upper and lower level sensors disposed to sense an upper and lower level of the medium within the chamber, respectively;
- valving means for selectively controlling flow of the second supply of medium from the chamber through the first and second ports;
- means for pressurizing the chamber at a second pressure and maintaining the second pressure independently of the first pressure; and
- wherein the delivery means alternatively raises the first pressure in the capillaries above the second pressure in the chamber when a low level of medium is sensed in the chamber and lowers the first pressure in the capillaries below the second pressure in the chamber when a high level of medium is sensed in the chamber, said raising and lowering of first pressure in the chamber being done in cooperation with the valving means so that circulation of medium within the extracapillary space is effected.

18. The device of claim 17 wherein the chamber is fluidly connected to the first and second ports of the shell by first and second conduits and wherein the valving means includes first and second valves restricting flow in the first and second conduits, respectively.

19. The device of claim 17 wherein the means for pressurizing the chamber includes a mechanism for delivering gas under pressure into the chamber.

20. The device of claim 17 wherein the permeable walls of the capillaries have a selective molecular weight cut-off of less than approximately 50,000 Daltons.

21. The device of claim 20 wherein the permeable walls of the capillaries have a selective molecular weight cut-off of less than approximately 15,000 Daltons.

* * * * *